(12) United States Patent
Saito

(10) Patent No.: US 11,284,852 B2
(45) Date of Patent: Mar. 29, 2022

(54) RADIATION IMAGING APPARATUS, RADIATION IMAGING SYSTEM, METHOD OF CONTROLLING RADIATION IMAGING APPARATUS, AND NON-TRANSITORY COMPUTER-READABLE STORAGE MEDIUM

(71) Applicant: CANON KABUSHIKI KAISHA, Tokyo (JP)

(72) Inventor: Hidehiko Saito, Saitama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/576,225

(22) Filed: Sep. 19, 2019

(65) Prior Publication Data

US 2020/0096654 A1    Mar. 26, 2020

(30) Foreign Application Priority Data

Sep. 26, 2018   (JP) .............................. JP2018-180940

(51) Int. Cl.
| | |
|---|---|
| *A61B 6/00* | (2006.01) |
| *G01T 1/20* | (2006.01) |
| *H04N 5/32* | (2006.01) |
| *H04N 5/367* | (2011.01) |
| *G01T 1/24* | (2006.01) |

(52) U.S. Cl.
CPC .......... *A61B 6/5258* (2013.01); *A61B 6/4233* (2013.01); *G01T 1/2018* (2013.01); *G01T 1/247* (2013.01); *H04N 5/32* (2013.01); *H04N 5/3675* (2013.01)

(58) Field of Classification Search
None
See application file for complete search history.

(56) References Cited

U.S. PATENT DOCUMENTS

| | | | | |
|---|---|---|---|---|
| 8,208,046 | B2* | 6/2012 | Ogino | .................... H04N 5/365 |
| | | | | 348/246 |
| 9,838,619 | B2 | 12/2017 | Yamazaki et al. | |
| 10,104,323 | B2* | 10/2018 | Maruyama | ................ G06T 5/20 |
| 10,425,602 | B2* | 9/2019 | Maruyama | ............. H04N 1/409 |

(Continued)

FOREIGN PATENT DOCUMENTS

| | | |
|---|---|---|
| JP | 2009-273630 A | 11/2009 |
| JP | 2010-263961 A | 11/2010 |
| JP | 2011-019591 | 2/2011 |

*Primary Examiner* — Thomas R Artman
(74) *Attorney, Agent, or Firm* — Venable LLP

(57) ABSTRACT

A radiation imaging apparatus is provided. The apparatus comprises: an imaging unit including a plurality of pixels configured to convert incident radiation into an electrical signal; a storage unit configured to store position information of a first pixel, among the pixels, which always outputs an abnormal pixel value; a correction unit configured to detect a second pixel, among the pixels, which is not stored in the storage unit and outputs an abnormal pixel value, and correct the pixel value of the second pixel; and an interpolation unit configured to, after image data output from the imaging unit is processed by the correction unit, generate a pixel value of the first pixel based on the position information and a pixel value of a pixel, among the pixels, which is arranged near the first pixel.

8 Claims, 7 Drawing Sheets

(56) References Cited

U.S. PATENT DOCUMENTS

| | | | |
|---|---|---|---|
| 2005/0078204 A1* | 4/2005 | Matsuoka | H04N 5/3675 348/247 |
| 2008/0056606 A1* | 3/2008 | Kilgore | F41G 7/2253 382/275 |
| 2008/0117318 A1* | 5/2008 | Aoki | H04N 5/367 348/246 |
| 2010/0073526 A1* | 3/2010 | Watanabe | H04N 5/367 348/247 |
| 2011/0080505 A1* | 4/2011 | Ogino | H04N 5/365 348/246 |
| 2012/0020541 A1 | 1/2012 | Hayashida | |
| 2013/0327950 A1 | 12/2013 | Niwa et al. | |
| 2018/0115728 A1 | 4/2018 | Maruyama et al. | |
| 2020/0096654 A1* | 3/2020 | Saito | H04N 5/32 |

* cited by examiner

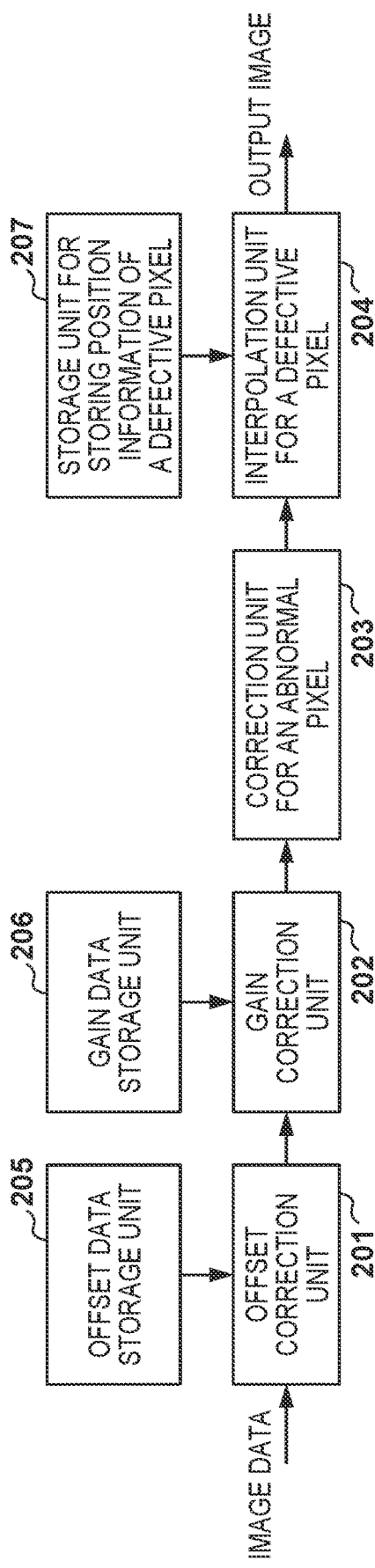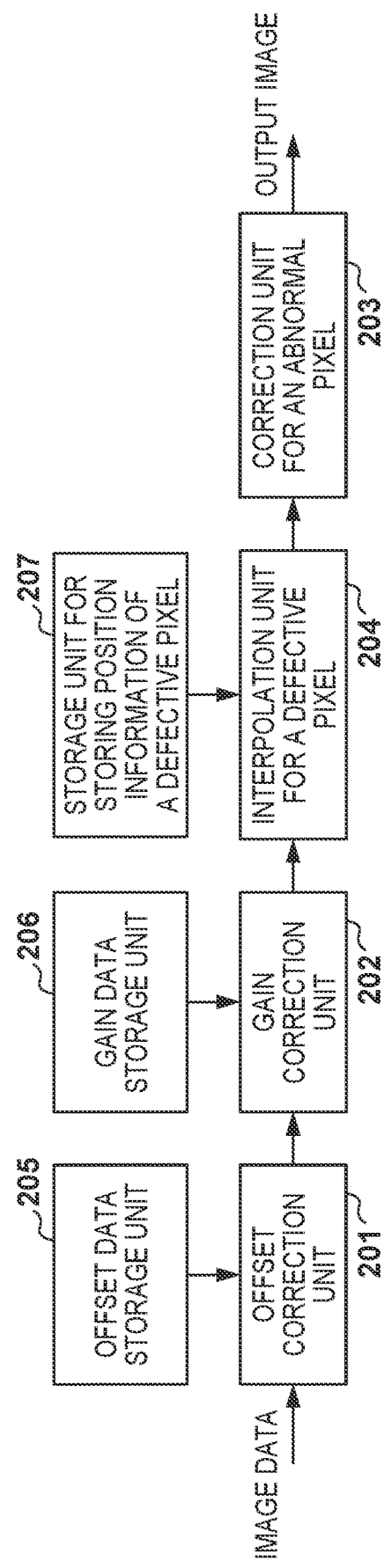

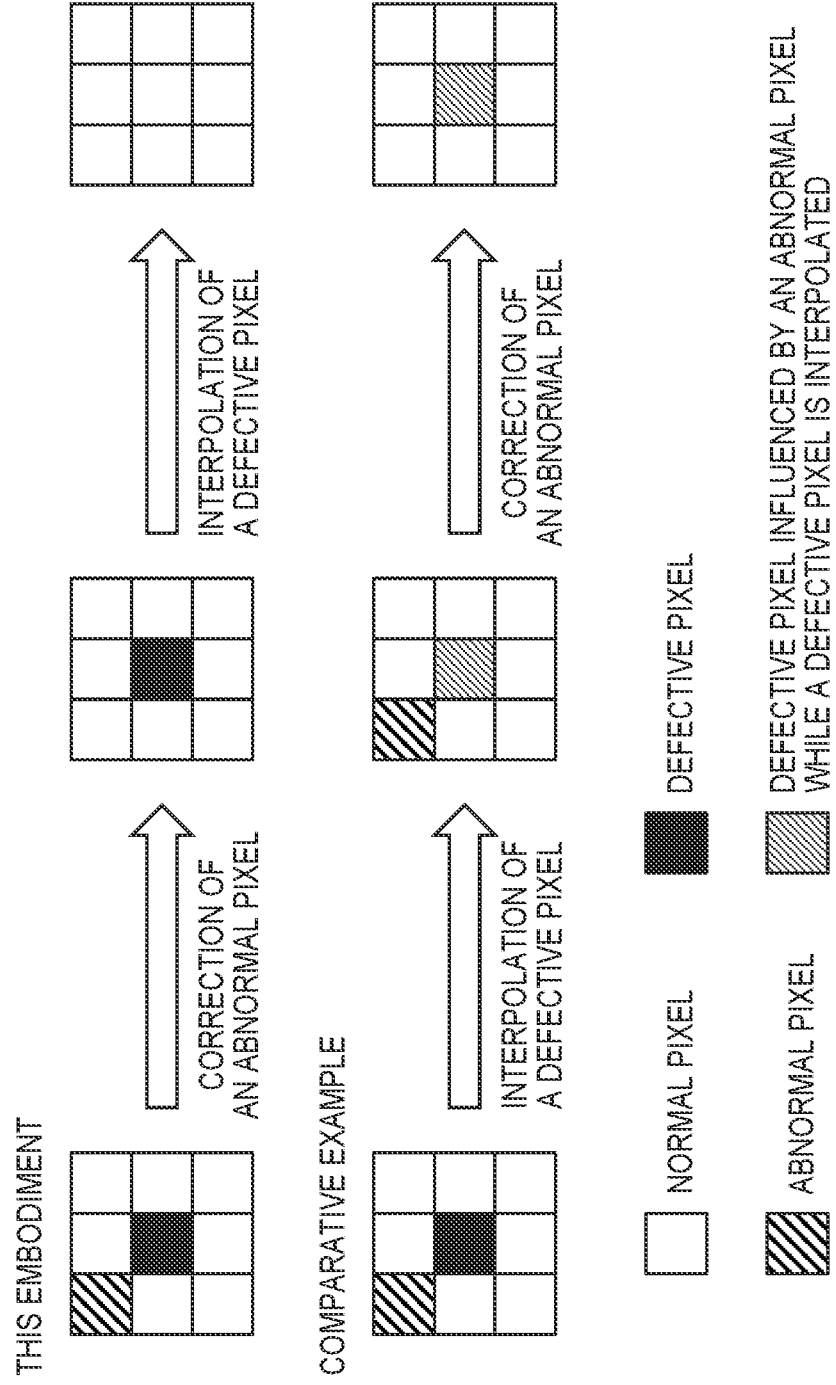

FIG. 5A 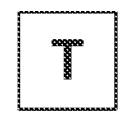 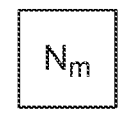

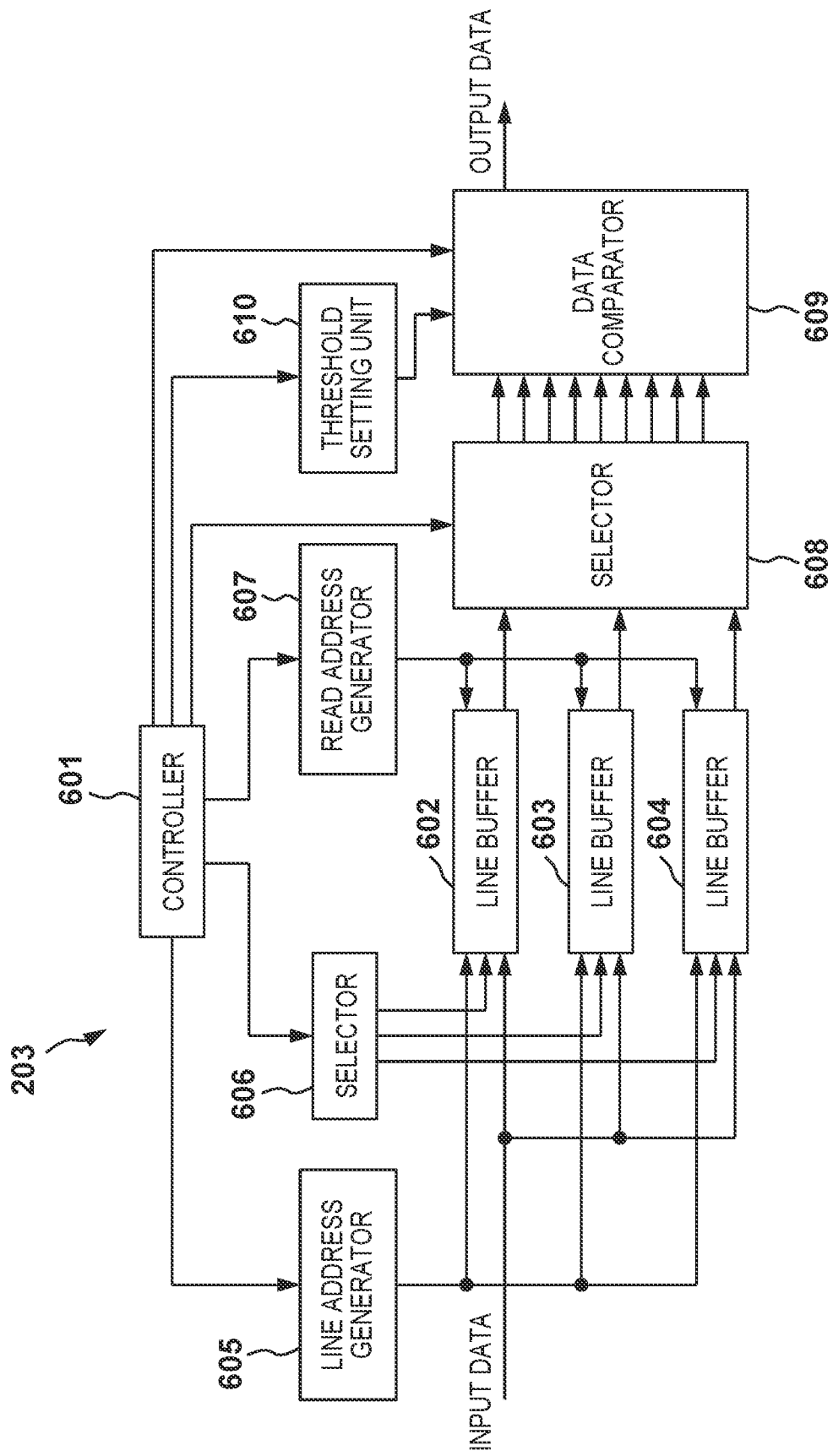

RADIATION IMAGING APPARATUS, RADIATION IMAGING SYSTEM, METHOD OF CONTROLLING RADIATION IMAGING APPARATUS, AND NON-TRANSITORY COMPUTER-READABLE STORAGE MEDIUM

BACKGROUND OF THE INVENTION

Field of the Invention

The present invention relates to a radiation imaging apparatus, a radiation imaging system, a method of controlling the radiation imaging apparatus, and a non-transitory computer-readable storage medium.

Description of the Related Art

As an imaging apparatus for use in a medical image diagnosis or nondestructive inspection using radiation, a radiation imaging apparatus using an FPD (Flat Panel Detector) formed by using a semiconductor material is known. A radiation imaging apparatus like this is used as a digital imaging apparatus for still images or moving images in, for example, a medical image diagnosis.

A pixel (defective pixel) that always outputs an abnormal signal sometimes exists among a plurality of pixels arranged in the FPD. Also, a pixel that temporarily outputs an abnormal signal due to the mixing of incidental noise or the like during imaging sometimes exists. Japanese Patent Laid-Open No. 2010-263961 discloses an X-ray image capturing apparatus that interpolates the pixel value of a defective pixel having preregistered position information in captured image data and then corrects the pixel value of a pixel that temporarily outputs an abnormal signal.

SUMMARY OF THE INVENTION

When interpolating the pixel value of a defective pixel by using the pixel values of pixels arranged near the defective pixel, there is the possibility that a pixel that temporarily outputs an abnormal signal due to noise or the like during imaging exists near the defective pixel. If a pixel that temporarily outputs an abnormal signal exists near a defective pixel, the pixel value of the pixel that temporarily outputs an abnormal signal is used in interpolation of the pixel value of the defective pixel. This decreases the accuracy of interpolation of the pixel value of the defective pixel, and an artifact may occur.

An embodiment of the present invention provides a technique advantageous in suppressing an artifact.

According to some embodiments, a radiation imaging apparatus comprising: an imaging unit including a plurality of pixels configured to convert incident radiation into an electrical signal; a storage unit configured to store position information of a first pixel, among the plurality of pixels, which always outputs an abnormal pixel value; a correction unit configured to detect a second pixel, among the plurality of pixels, which is not stored in the storage unit and outputs an abnormal pixel value, and correct the pixel value of the second pixel; and an interpolation unit configured to, after image data output from the imaging unit is processed by the correction unit, generate a pixel value of the first pixel based on the position information and a pixel value of a pixel, among the plurality of pixels, which is arranged near the first pixel, is provided.

According to some other embodiments, a method of controlling a radiation imaging apparatus comprising an imaging unit including a plurality of pixels configured to convert incident radiation into an electrical signal, wherein the radiation imaging apparatus further comprises: a storage unit configured to store position information of a first pixel, among the plurality of pixels, which always outputs an abnormal pixel value; an interpolation unit configured to generate a pixel value of the first pixel based on the position information and a pixel value of a pixel, among the plurality of pixels, which is arranged near the first pixel; and a correction unit configured to detect a second pixel, among the plurality of pixels, which is not stored in the storage unit and outputs an abnormal pixel value, and correct the pixel value of the second pixel, and the method comprises: performing processing of the correction unit on image data output from the imaging unit; and performing processing of the interpolation unit on the image data processed by the correction unit, is provided.

According to still other embodiments, a radiation imaging apparatus comprising: an imaging unit including a plurality of pixels for converting incident radiation into an electrical signal; a storage unit configured to store position information of a first pixel, among the plurality of pixels, which always outputs an abnormal pixel value; a correction unit configured to detect a second pixel, among the plurality of pixels, which is not stored in the storage unit and outputs an abnormal pixel value, and correct the pixel value of the second pixel; and an interpolation unit configured to generate, for image data output from the imaging unit and processed by the correction unit, a pixel value of the first pixel based on the position information and a pixel value of a pixel, among the plurality of pixels, which is arranged near the first pixel, is provided.

Further features of the present invention will become apparent from the following description of exemplary embodiments (with reference to the attached drawings).

BRIEF DESCRIPTION OF THE DRAWINGS

FIG. 2 is a block diagram showing an image data processing method of the radiation imaging apparatus shown in FIG. 1;

FIG. 3 is a block diagram showing an image data processing method of a comparative example;

FIG. 4 is a view for explaining an artifact caused by the processing order of image data;

FIGS. 5A to 5E are views showing examples of an abnormal signal correction method of the radiation imaging apparatus shown in FIG. 1;

FIG. 6 is a view showing a configuration example of a correction unit of the radiation imaging apparatus shown in FIG. 1;

DESCRIPTION OF THE EMBODIMENTS

Figure 1:
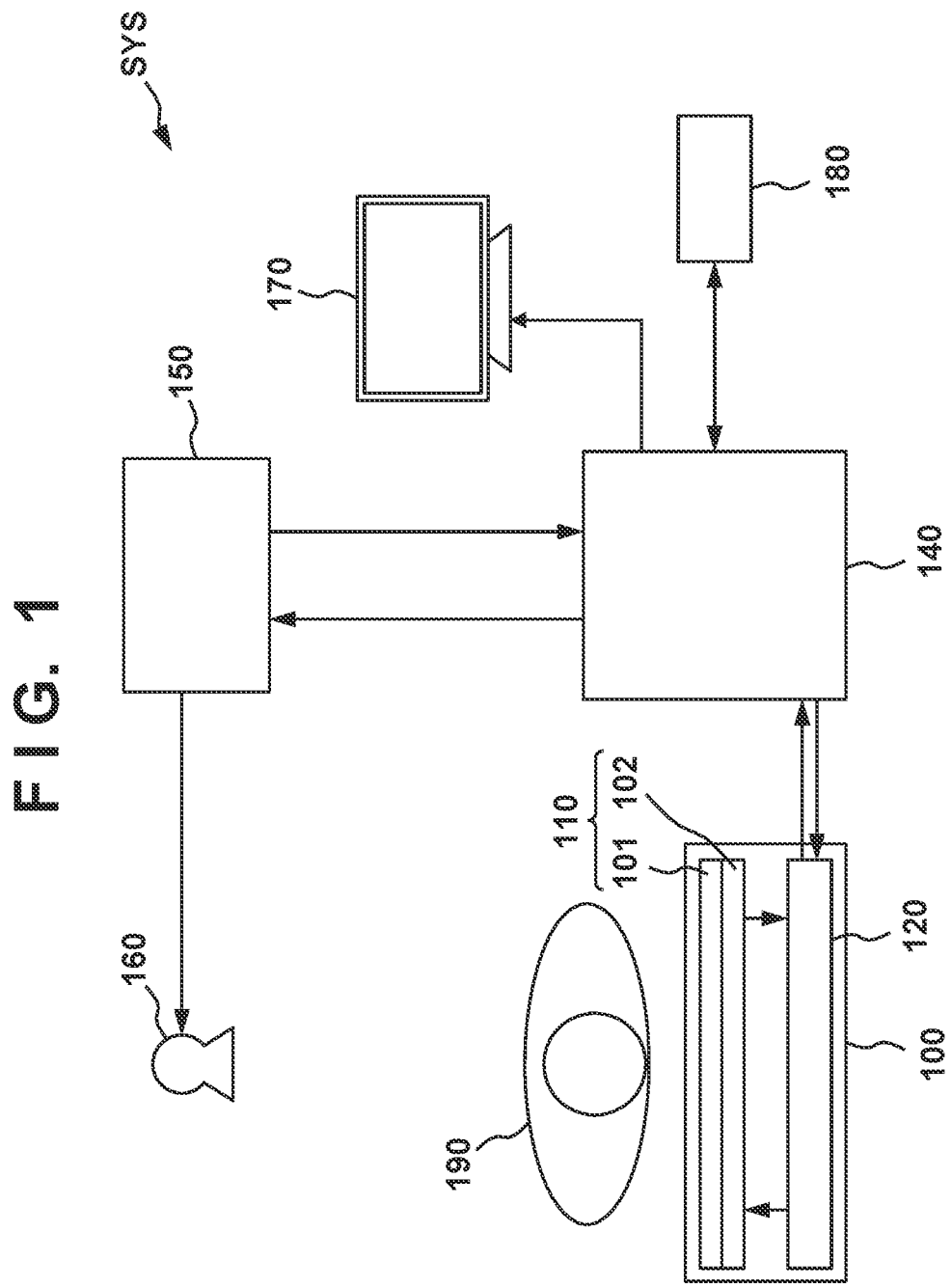
FIG. 1 is a view showing a configuration example of a radiation imaging system using a radiation imaging apparatus according to an embodiment of the present invention.

Practical embodiments of a radiation imaging apparatus according to the present invention will be explained below with reference to the accompanying drawings. In the following explanation and drawings, common reference numerals denote common parts throughout a plurality of drawings. Therefore, the common parts will be explained by mutually referring to the plurality of drawings, and an explanation of the parts denoted by the common reference numerals will be omitted as needed. In addition, radiation in the present invention includes beams that form particles (including photons) released by radioactive decay, such as α-ray, β-ray, and γ-ray, and can also include beams having energies equal to or higher than those of the above beams, such as X-ray, a particle beam, and cosmic ray.

The arrangements and operations of radiation imaging apparatuses according to embodiments of the present invention will be explained with reference to FIGS. 1 to 6. FIG. 1 is a view showing the configuration of a radiation imaging system SYS using a radiation imaging apparatus 100 according to the first embodiment of the present invention. The radiation imaging system SYS includes the radiation imaging apparatus 100, a control computer 140, a radiation source controller 150, and a radiation source 160.

The radiation source 160 generates radiation in accordance with a control signal output from the radiation source controller 150, and emits the radiation toward the radiation imaging apparatus 100. The radiation emitted from the radiation source 160 enters the radiation imaging apparatus 100 through a subject 190. The radiation imaging apparatus 100 generates an image corresponding to the emitted radiation dose, and transmits the image to the control computer 140. The control computer 140 controls the operation of the whole radiation imaging system SYS. For example, the control computer 140 instructs the radiation source controller 150 to start and stop the emission of radiation, and notifies the radiation imaging apparatus 100 of the start and stop of the emission of radiation, thereby synchronizing the radiation source controller 150 and the radiation imaging apparatus 100. The control computer 140 may also be used by the user (a doctor or a radiologist) to change the settings of the radiation imaging apparatus 100. The control computer 140 may incorporate a display and a keyboard with which the user confirms or inputs the conditions of radiation to be generated by the radiation source 160 and the settings of the radiation imaging apparatus 100. Furthermore, as in the configuration shown in FIG. 1, a display unit 170 by which the user confirms various conditions and settings and a console 180 by which the user inputs various conditions and settings may also be arranged in addition to the control computer 140.

The radiation imaging apparatus 100 includes an imaging unit 110 and a control unit 120. The imaging unit 110 includes a scintillator 101, and an imaging panel 102 on which a plurality of pixels each including a photoelectric converter for converting light, which is converted from radiation by the scintillator 101, into an electrical signal are arranged. The imaging unit 110 includes the scintillator 101 and the imaging panel 102 in this embodiment, but the present invention is not limited to this. The imaging unit 110 may also be configured by an imaging panel on which a plurality of pixels each including a conversion element for directly converting incident radiation into an electrical signal are arranged, without using the scintillator 101. The imaging unit 110 need only include a plurality of pixels each of which converts incident radiation into an electrical signal corresponding to the dose of the incident radiation.

The control unit 120 controls the whole radiation imaging apparatus 100. The control unit 120 can have a regulator function of receiving electric power from an external power supply or a built-in battery, and supplying the electric power to the whole radiation imaging apparatus 100. Also, the control unit 120 drives the imaging panel 102, and reads out image data from the imaging panel 102. Furthermore, the control unit 120 performs a correction process of correcting the characteristics unique to the imaging panel 102, for the image data read out from the imaging panel 102. Examples of the correction process to be performed by the control unit 120 are offset correction and gain correction. As will be described in detail later, other examples of the correction process to be performed by the control unit 120 are interpolation for a pixel that always outputs an abnormal signal, and correction for a pixel that temporarily outputs an abnormal signal due to the mixing of incidental noise or the like during imaging. The control computer 140 can also include these correction functions. In this case, "the radiation imaging apparatus" of the present invention can be obtained by combining the correction functions of the radiation imaging apparatus 100 and those of the control computer 140.

The correction process of the control unit 120 will be explained in detail below. FIG. 2 is a block diagram showing the method of the image data correction process of the radiation imaging apparatus 100. To perform the correction process, the control unit 120 includes an offset correction unit 201 for correcting offset, and a gain correction unit 202 for correcting gain. The control unit 120 also includes a correction unit 203 for correcting a pixel (a second pixel: to be called an abnormal pixel in some cases hereinafter) that temporarily outputs an abnormal signal due to incidental noise or the like, and an interpolation unit 204 for interpolating a pixel (a first pixel: to be called a defective pixel in some cases hereinafter) that always outputs an abnormal signal. The control unit 120 further includes a storage unit 207 for storing position information of a defective pixel that always outputs an abnormal pixel value, among the plurality of pixels. The position information of a defective pixel is obtained by, for example, a test before the shipment of the radiation imaging apparatus 100 or a calibration work after the shipment, and prestored in the storage unit 207.

The occurrence of an artifact in a correction process of a comparative example will be explained first, and then the correction process of this embodiment will be explained. FIG. 3 is a block diagram showing the method of the correction process of the comparative example.

First, the offset correction unit 201 performs a process of correcting the offset of image data read out from the imaging panel 102, by using offset data stored in an offset data storage unit 205. As this offset data, a signal output from each pixel of the imaging panel 102 in a state in which no radiation is emitted, for example, before imaging, is obtained and stored in the offset data storage unit 205. Then, the gain correction unit 202 performs a process of correcting the gain of the image data processed by the offset correction unit 201, by using gain data corresponding to the imaging conditions or the like and stored in a gain data storage unit 206.

Subsequently, the interpolation unit 204 performs a spatial interpolation process on the image data processed by the gain correction unit 202, based on the position information of a defective pixel registered in the storage unit 207. More specifically, the interpolation unit 204 generates a pixel value of a defective pixel, based on the position information of the defective pixel stored in the storage unit 207 and the pixel value of a pixel arranged near the defective pixel among the plurality of pixels arranged on the imaging panel 102. The interpolation unit 204 sets the generated pixel value as the pixel value of the defective pixel. A defective pixel that always outputs an abnormal signal always outputs an abnormal signal due to, for example, a problem of the manufacturing process of the imaging panel 102 or deterioration with time. Therefore, the defective pixel is a pixel whose position information can be prestored in the storage unit 207. The defective pixel can be, for example, a pixel that always outputs the same pixel value regardless of the dose of incident radiation.

The correction unit 203 corrects an abnormal pixel of the image data processed by the interpolation unit 204. More specifically, the correction unit 203 detects an abnormal pixel that is not stored in the storage unit 207 and outputs an abnormal pixel value, from among the plurality of pixels, and corrects the pixel value of the abnormal pixel. An abnormal pixel that temporarily outputs an abnormal signal is a pixel having a pixel value that randomly shows an abnormal value both spatially and temporally due to the mixing of incidental noise or the like during imaging. For example, an abnormal pixel can be formed when an impact is applied to the radiation imaging apparatus 100 during imaging. Also, in the configuration using the scintillator 101 as in this embodiment, a radiation photon having passed through the scintillator 101 without being absorbed (converted into light) by it sometimes enters the imaging panel 102. If this radiation photon causes a photoelectric effect in the photoelectric converter of a pixel of the imaging panel 102 and is converted into an electrical signal, the pixel may output an abnormally large pixel value. Generally, an abnormal pixel supposedly outputs a pixel value larger than that of a normal pixel. An abnormal pixel like this cannot be registered in the storage unit 207. Therefore, the correction unit 203 detects a pixel that outputs an abnormal pixel value from pixels not stored in the storage unit 207, and corrects the pixel value. The image data processed by the correction unit 203 is transferred as an output image to the control computer 140.

Next, the occurrence of an artifact in the comparative example will be explained with reference to FIG. 4. FIG. 4 is a view for explaining the occurrence of an artifact caused by the image data processing order of the correction unit 203 and the interpolation unit 204. The lower row of FIG. 4 shows the correction process of the comparative example.

After the offset correction and the gain correction, the interpolation unit 204 first performs a spatial correction process of determining the pixel value of a defective pixel by an interpolation calculation by using the pixel values of pixels arranged near the defective pixel. In this process, if an abnormal pixel exists near the defective pixel, the interpolation unit 204 interpolates the defective pixel by using pixels including the abnormal pixel, because the abnormal pixel is not registered in the storage unit 207. Accordingly, the defective pixel may not sufficiently be corrected. As described above, an abnormal pixel can output a pixel value larger than that of a normal pixel. For example, a signal charge to be generated when a radiation photon is directly converted into an electrical signal by the photoelectric converter is larger by about 10 times than that to be generated when light converted by the scintillator 101 is detected. Therefore, even after the interpolation unit 204 interpolates the defective pixel, an abnormal pixel value caused by the abnormal pixel existing near the defective pixel may remain in the defective pixel. As described previously, an abnormal pixel generally outputs a pixel value larger than that of a normal pixel. If an abnormal pixel exists near the defective pixel, therefore, it is highly likely that the pixel value of the interpolated defective pixel becomes larger than the original pixel value. That is, the pixel value of the defective pixel is influenced by an abnormal pixel while the defective pixel is interpolated. In correction to be performed by the correction unit 203 following the processing in the interpolation unit 204, a defective pixel whose position information is stored in the storage unit 207 is not corrected. As a consequence, the accuracy of interpolation of the pixel value of the defective pixel decreases, and an artifact may occur.

On the other hand, in this embodiment as shown in FIG. 2, image data output from the imaging unit 110 is processed by the correction unit 203 and then processed by the interpolation unit 204. In other words, the interpolation unit 204 performs the defective pixel interpolating process on the image data output from the imaging unit 110 and having undergone the process of correcting the pixel value of an abnormal pixel performed by the correction unit 203. This will be explained by using the upper row of FIG. 4. First, the correction unit 203 corrects an abnormal pixel. Then, the interpolation unit 204 corrects a defective pixel. Even when an abnormal pixel exists near a defective pixel, therefore, the influence of the pixel value of the abnormal pixel is suppressed in a spatial correction process of determining a pixel value by an interpolation calculation by using the pixel values of pixels arranged near the defective pixel. Consequently, the occurrence of an artifact in the correction process by the radiation imaging apparatus 100 is suppressed, and the reliability of a radiation image to be generated can be improved.

Figure 5B:
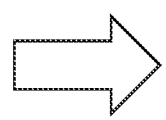

The method of correcting an abnormal pixel by the correction unit 203 will be explained below with reference to FIGS. 5A to 5E. Referring to FIG. 5A, T indicates an abnormal pixel. The correction unit 203 can correct the pixel value of the abnormal pixel T based on, for example, the pixel value of a nearby pixel $N_m$, which is arranged near the abnormal pixel T, of the plurality of pixels. As shown in FIG. 5A, the nearby pixel $N_m$ can be eight pixels (nearby pixels $N_1$ to $N_8$) surrounding the abnormal pixel T. The nearby pixel $N_m$ can also be four pixels (for example, the nearby pixels $N_2$, $N_4$, $N_5$, and $N_7$) adjacent to the abnormal pixel T. The nearby pixel $N_m$ can further be 24 pixels included in a 5×5 matrix surrounding the abnormal pixel T twice. In this specification, an explanation will be simplified by assuming that the eight pixels surrounding the abnormal pixel T are the nearby pixels $N_m$. Also, an explanation will be made by assuming that the pixels output pixel values from 1 to 9.

As shown in FIG. 5B, the correction unit 203 can correct the pixel value of the abnormal pixel T to the same pixel value as that of one of the nearby pixels $N_m$, which outputs the largest pixel value. That is, when the pixels output pixel values shown in FIG. 5B, the correction unit 203 corrects the pixel value of the abnormal pixel T to that of the nearby pixel $N_7$.

Figure 5C:
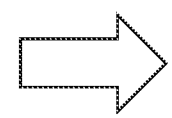

Also, as shown in FIG. 5C, the correction unit 203 can correct the pixel value of the abnormal pixel T to the same pixel value as that of one of the nearby pixels $N_m$, which outputs the second largest pixel value. That is, when the pixels output pixel values shown in FIG. 5C, the correction unit 203 corrects the pixel value of the abnormal pixel T to that of the nearby pixel $N_6$. Accordingly, even when the nearby pixels $N_m$ surrounding the abnormal pixel T further include an abnormal pixel in which a radiation photon is directly converted into an electrical signal by the photoelectric converter, the abnormal pixel T can appropriately be corrected. In addition, even when the nearby pixels $N_m$ surrounding the abnormal pixel T include a defective pixel having an abnormally large pixel value, this method can properly correct the abnormal pixel T.

The possibility that the photoelectric converter arranged in each pixel of the imaging panel 102 directly converts a radiation photon into an electrical signal (this will be called direct conversion) in the imaging unit 110 using the scintillator 101 will be explained below. Since this direct conversion occurs when the photoelectric converter absorbs radiation transmitted through the scintillator 101, the occurrence frequency can be estimated based on the dose of radiation having entered the scintillator 101, the thickness of the scintillator 101, the quantum efficiency of the photoelectric converter, and the like. Assume that the scintillator 101 is made of 1,000-µm thick CsI, the photoelectric converter is made of Si, and the radiation is X-ray. In this case, about 20% of X-ray having entered the scintillator 101 is transmitted through the scintillator 101, and the photoelectric converter (Si has almost no sensitivity to light having a wavelength on the order of pm) directly converts less than 1% of the transmitted X-ray. Even when using the method shown in FIG. 5B, therefore, the probability of the generation of another abnormal pixel in the nearby pixels $N_m$ is low, so the abnormal pixel T can be corrected. This can suppress the occurrence of an artifact compared to a case in which a defective pixel is corrected first.

A case in which the nearby pixels $N_m$ surrounding the abnormal pixel T include a defective pixel will be explained. In this case, the pixel value of this defective pixel can take a value from 1 to 9. When using the method shown in FIG. 5B or 5C, therefore, it is in many cases possible to appropriately correct the abnormal pixel T, unless the defective pixel is a pixel that always outputs a large pixel value. Furthermore, when the correction unit 203 obtains the position information of a defective pixel from the storage unit 207 and the nearby pixels $N_m$ include a defective pixel, image data can be corrected based on the pixel values of the nearby pixels $N_m$ excluding the defective pixel. This can further suppress the occurrence of an artifact.

Figure 5D:
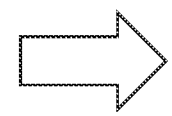
Figure 5E:
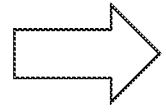

The abnormal pixel correcting method to be performed by the correction unit 203 is not limited to these methods. For example, as shown in FIG. 5D, the correction unit 203 may also correct the pixel value of the abnormal pixel T to the average value of the pixel values of the nearby pixels $N_m$. That is, when the pixels output pixel values shown in FIG. 5D, the correction unit 203 corrects the pixel value of the abnormal pixel T to the average value of the pixel values of the nearby pixels $N_1$ to $N_8$. By using the average value of the pixel values of a plurality of pixels, even when the nearby pixels $N_m$ include a defective pixel or another abnormal pixel, it is possible to suppress the influence of these defective pixels on the correction of the abnormal pixel. Furthermore, when the correction unit 203 obtains the position information of a defective pixel from the storage unit 207 and the nearby pixels $N_m$ include a defective pixel, the correction unit 203 may also obtain the average value based on the pixel values of the nearby pixels $N_m$ excluding the defective pixel.

In addition, the correction of the abnormal pixel T to be performed by the correction unit 203 is not limited to spatial correction using pixels arranged near the abnormal pixel T as described above. For example, when continuously performing imaging such as imaging of a moving image, the correction unit 203 can correct the abnormal pixel T by using the pixel values of pixels in the same position as that of the abnormal pixel T, in frames before and after a frame containing the abnormal pixel T. For example, the correction unit 203 can correct the pixel value of the abnormal pixel T to the same pixel value as that in an immediately preceding frame or an immediately succeeding frame. As another example, the correction unit 203 can correct the pixel value of the abnormal pixel T based on the average value of a pixel value in an immediately preceding frame and a pixel value in an immediately succeeding frame, that is, based on pixel values in two or more frames.

As a method of detecting an abnormal pixel, the correction unit 203 can detect, as an abnormal pixel, a pixel that outputs a pixel value equal to or larger than a set threshold, from among the plurality of pixels. In this case, the correction unit 203 can include a threshold setting unit for setting the threshold. For example, the threshold setting unit can set an appropriate threshold in accordance with the processing of the offset correction unit 201 or the gain correction unit 202. In addition, when the user sets the irradiation conditions (for example, the X-ray tube voltage and irradiation time of the radiation source 160) or the imaging conditions such as a portion to be imaged, the user can set the threshold by using the threshold setting unit, or the threshold setting unit can set an appropriate threshold in accordance with the imaging conditions set by the user. For example, when the threshold is set at 9, a pixel in the center of the matrix shown in FIG. 5E outputs a pixel value of 8, so this pixel is not detected as an abnormal pixel, and the correction unit 203 performs no correction.

FIG. 6 is a view showing a configuration example of the correction unit 203 of the radiation imaging apparatus 100. The correction unit 203 includes a controller 601 for controlling the operation of the correction unit, line buffers 602, 603, and 604, a line address generator 605, selectors 606 and 608, a read address generator 607, a threshold setting unit 610, and a data comparator 609. The line buffers 602, 603, and 604 save image data supplied to the correction unit line by line. The line address generator 605 controls write of the image data to one of the line buffers 602, 603, and 604. The selector 606 selects a save destination of image data for each line. The read address generator 607 controls an address for reading out the image data from the line buffers 602, 603, and 604. The selector 608 rearranges the image data read out from the line buffers 602, 603, and 604 into a 3×3 matrix array as shown in FIG. 5A. The threshold setting unit 610 sets the threshold for detecting an abnormal pixel as described above. The data comparator 609 compares the abnormal pixel T with the nearby pixels $N_1$ to $N_8$ based on data of pixel values arranged into the 3×3 matrix by the selector 608, and corrects the pixel value of the abnormal pixel T in accordance with the pixel values of the nearby pixels $N_1$ to $N_8$.

The controller 601 of the correction unit 203 can be configured to be able to correct the pixel value of the abnormal pixel T by using a method selected from at least two types as described above. In this case, the controller 601 of the correction unit 203 can further include a method setting unit for selecting a method. The method selecting unit can select a correction method in accordance with user's designation, and can also select a correction method in accordance with the above-described imaging conditions for performing imaging. For example, when irradiation conditions that increase the possibility that radiation is transmitted through the scintillator 101 and converted into an electric charge signal by the photoelectric converter of the imaging panel 102 are selected, the method shown in FIG. 5C can be selected.

Input data supplied from the gain correction unit 202 are sequentially stored in the line buffers 602, 603, and 604 line by line by the line address generator 605 and the selector 606. Then, the read address generator 607 and the selector 608 select nine pixels of the 3×3 matrix. The data comparator 609 detects the abnormal pixel T from the nine pixels by using the threshold set by the threshold setting unit 610.

Also, the data comparator 609 corrects the pixel value of the abnormal pixel T in accordance with the pixel values of the nearby pixels $N_m$ by using the method selected by the method selecting unit of the controller 601, and outputs the corrected pixel value as output data to the interpolation unit 204.

Since the radiation imaging apparatus 100 has the configuration explained above, the occurrence of an artifact caused by an abnormal pixel that is generated at random both temporally and spatially is suppressed. As a consequence, the reliability of a radiation image obtained by the radiation imaging apparatus 100 improves.

Figure 7:
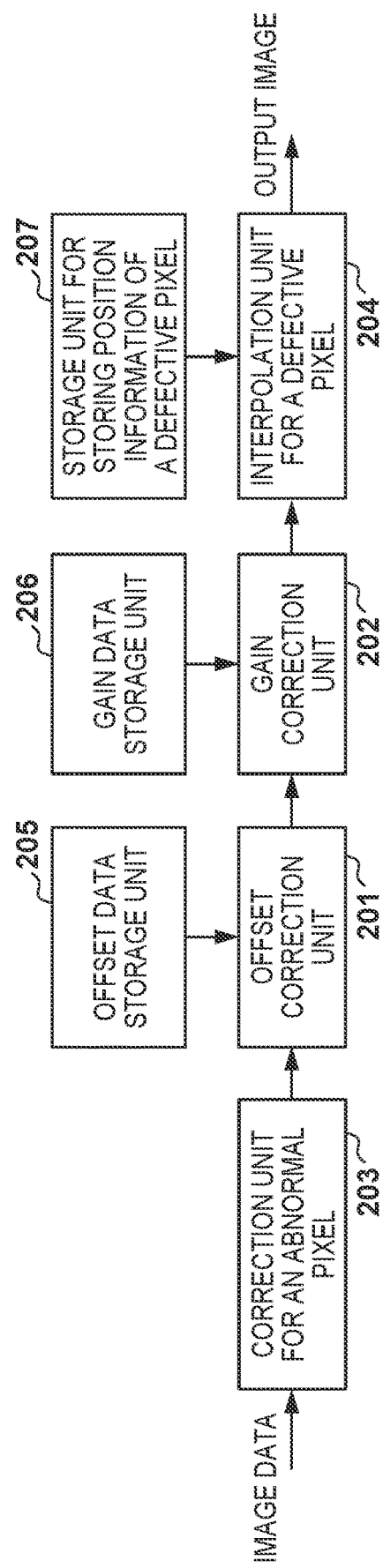
FIG. 7 is a block diagram showing a modification of the processing method shown in FIG. 2.

The configuration and operation of a radiation imaging apparatus according to an embodiment of the present invention will be explained with reference to FIGS. 7 and 8. FIG. 7 is a block diagram showing the method of an image data correction process of a radiation imaging apparatus 100 according to the second embodiment of the present invention. The difference from the block diagram of the first embodiment shown in FIG. 2 is that the processes by an offset correction unit 201 and a gain correction unit 202 are performed after the process by a correction unit 203 is performed. Therefore, the configuration of the radiation imaging apparatus 100 can be the same as that of the above-described first embodiment except the arrangement of the correction unit 203 to be explained below.

Figure 8:
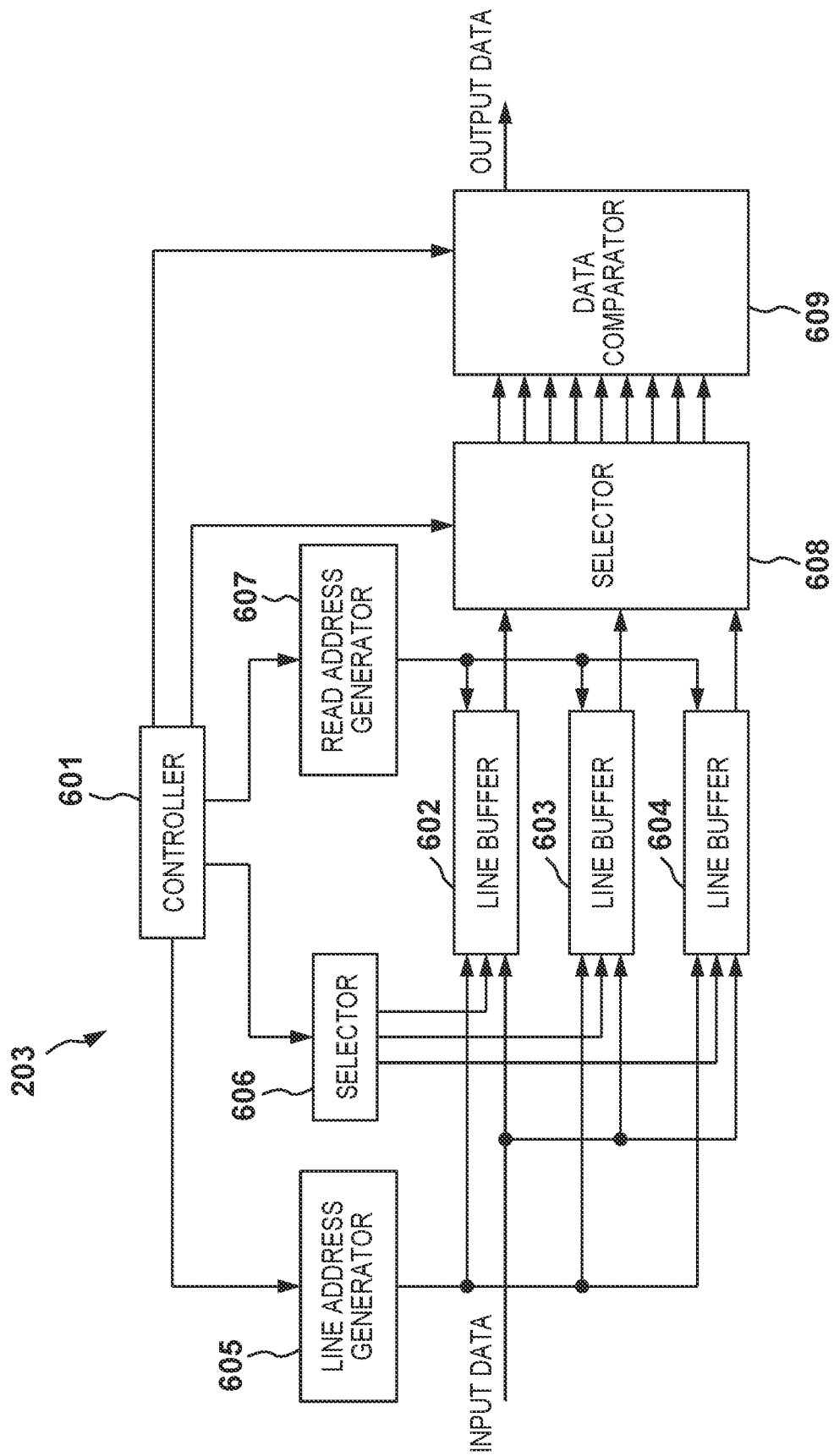
FIG. 8 is a view showing a modification of the correction unit shown in FIG. 6.

FIG. 8 is a view showing a configuration example of the correction unit 203 of the radiation imaging apparatus 100 according to this embodiment. As described previously, the pixel value of an abnormal pixel can be a maximum value of pixel values set in the radiation imaging apparatus 100. However, the pixel value of an abnormal pixel processed by the offset correction unit 201 and the gain correction unit 202 is a corrected value processed by the gain correction unit 202. Accordingly, the pixel value of an abnormal pixel changes in accordance with the imaging conditions, so the threshold for detecting an abnormal pixel must be changed to a proper value corresponding to the offset correction and the gain correction for every imaging conditions.

On the other hand, in this embodiment, the first step of the process of correcting image data supplied from an imaging panel 102 is the correction of an abnormal pixel by the correction unit 203. In image data supplied to the correction unit 203, the pixel value of an abnormal pixel can be the largest pixel value set in the radiation imaging apparatus 100. The threshold for detecting an abnormal pixel can be fixed by performing processing by arranging the correction unit 203 for detecting and correcting an abnormal pixel before the offset correction unit 201 and the gain correction unit 202. Compared to the correction unit 203 of the first embodiment shown in FIG. 6, therefore, the threshold setting unit 610 is omitted from the correction unit 203 of this embodiment shown in FIG. 8, and this further simplifies the arrangement.

As in the first embodiment described above, the arrangement of this embodiment suppresses the occurrence of an artifact caused by an abnormal pixel that is generated at random both temporally and spatially. Consequently, the reliability of a radiation image to be obtained by the radiation imaging apparatus 100 can be improved.

Other Embodiments

Embodiment(s) of the present invention can also be realized by a computer of a system or apparatus that reads out and executes computer executable instructions (e.g., one or more programs) recorded on a storage medium (which may also be referred to more fully as 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-180940, filed Sep. 26, 2018, which is hereby incorporated by reference herein in its entirety.

What is claimed is:

1. A radiation imaging apparatus, comprising:
   an imaging unit including a plurality of pixels configured to convert incident radiation into an electrical signal;
   a storage unit configured to store position information of a first pixel that outputs an abnormal pixel value;
   a correction unit configured to detect a second pixel that is different than the first pixel and outputs a pixel value not less than a set threshold among the plurality of pixels, and correct the pixel value of the second pixel; and
   an interpolation unit configured to generate a pixel value of the first pixel based on the position information and a pixel value of a pixel that is arranged near the first pixel after the correction unit processes image data output from the imaging unit, wherein
   the correction unit corrects the pixel value of the second pixel to a pixel value as that of a pixel which outputs a largest pixel value among pixels that are arranged nearby the second pixel.

2. The apparatus according to claim 1, wherein the imaging unit further includes a scintillator, and
   each of the plurality of pixels includes a photoelectric converter configured to convert light that is converted from radiation into an electrical signal by the scintillator.

3. A radiation imaging system, comprising:
   the radiation imaging apparatus according to claim 1; and
   a radiation source configured to emit radiation to the radiation imaging apparatus.

4. A radiation imaging apparatus, comprising:
   an imaging unit including a plurality of pixels configured to convert incident radiation into an electrical signal;

a storage unit configured to store position information of a first pixel that outputs an abnormal pixel value;

a correction unit configured to detect a second pixel that is different than the first pixel and outputs a pixel value not less than a set threshold among the plurality of pixels, and correct the pixel value of the second pixel; and an interpolation unit configured to generate a pixel value of the first pixel based on the position information and a pixel value of a pixel that is arranged near the first pixel after the correction unit processes image data output from the imaging unit, wherein the correction unit corrects the pixel value of the second pixel to a pixel value as that of a pixel which outputs a second largest pixel value among pixels that are arranged nearby the second pixel.

5. A radiation imaging apparatus, comprising:

an imaging unit including a plurality of pixels configured to convert incident radiation into an electrical signal;

a storage unit configured to store position information of a first pixel that outputs an abnormal pixel value;

a correction unit configured to detect a second pixel that is different than the first pixel and outputs a pixel value not less than a set threshold among the plurality of pixels, and correct the pixel value of the second pixel;

an interpolation unit configured to generate a pixel value of the first pixel based on the position information and a pixel value of a pixel that is arranged near the first pixel after the correction unit processes image data output from the imaging unit; and a method setting unit configured to select a method of correcting the pixel value of the second pixel including (i) correcting the pixel value of the second pixel to a pixel value as that of a pixel which outputs a largest pixel value among pixels that are arranged nearby the second pixel and (ii) correcting the pixel value of the second pixel to the same value as that of a pixel which outputs a second largest pixel value among the nearby pixels, wherein the correction unit is configured to correct the pixel value of the second pixel using the method selected by the method setting unit.

6. The apparatus according to claim 5, wherein the methods of correcting the pixel value of the second pixel further include (iii) correcting the pixel value of the second pixel to an average of the pixel values of the nearby pixels.

7. The apparatus according to claim 5, wherein the method setting unit selects the method in accordance with imaging conditions when performing imaging.

8. A radiation imaging apparatus, comprising:

an imaging unit including a plurality of pixels configured to convert incident radiation into an electrical signal;

a storage unit configured to store position information of a first pixel that outputs an abnormal pixel value;

a correction unit configured to detect a second pixel that is different than the first pixel and outputs a pixel value not less than a set threshold among the plurality of pixels, and correct the pixel value of the second pixel;

an interpolation unit configured to generate a pixel value of the first pixel based on the position information and a pixel value of a pixel that is arranged near the first pixel after the correction unit processes image data output from the imaging unit;

an offset correction unit configured to correct offset of the image data; and a gain correction unit configured to correct gain of the image data, wherein the offset correction unit corrects offset of the image data after performing processing by the correction unit and the gain correction unit corrects gain of the image data after performing processing by the correction unit.

* * * * *